United States Patent
Conley et al.

(10) Patent No.: US 9,925,025 B2
(45) Date of Patent: *Mar. 27, 2018

(54) CONTAINER FOR ORTHODONTIC APPLIANCES

(71) Applicant: 3M INNOVATIVE PROPERTIES COMPANY, St. Paul, MN (US)

(72) Inventors: Alan F. Conley, La Verne, CA (US); John A. Verdouw, Ontario, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/357,799

(22) Filed: Nov. 21, 2016

(65) Prior Publication Data
US 2017/0065388 A1    Mar. 9, 2017

Related U.S. Application Data

(63) Continuation of application No. 14/397,119, filed as application No. PCT/US2013/036998 on Apr. 17, 2013, now Pat. No. 9,504,544.
(Continued)

(51) Int. Cl.
*A61C 19/02* (2006.01)
*A61C 7/14* (2006.01)
*A61C 7/16* (2006.01)

(52) U.S. Cl.
CPC ............... *A61C 19/02* (2013.01); *A61C 7/14* (2013.01); *A61C 7/16* (2013.01); *A61C 2202/00* (2013.01); *A61C 2202/01* (2013.01)

(58) Field of Classification Search
CPC ....... A61C 19/02; A61C 7/16; A61C 2202/00; B65D 81/022
(Continued)

(56) References Cited

U.S. PATENT DOCUMENTS

| | | |
|---|---|---|
| 3,696,920 A | 10/1972 | Lahay |
| 3,918,581 A | 11/1975 | Scammon |

(Continued)

FOREIGN PATENT DOCUMENTS

| | | |
|---|---|---|
| EP | 2272459 | 1/2011 |
| JP | 01023947 | 1/1989 |

(Continued)

OTHER PUBLICATIONS

International Search Report for PCT International Application No. PCT/US2013/036998 dated Jul. 19, 2013, 2 pages.

*Primary Examiner* — Steven A. Reynolds

(57) ABSTRACT

Provided packaged orthodontic assemblies and methods compressively retain an orthodontic appliance in a container along opposing sides of the appliance adjacent the bonding surfaces of its base. This can be done using a mechanism that limits contact between the appliance and the container while accommodating a substantial range of transverse base dimensions. This engagement mechanism allows an adhesive-coated appliance to be retained in a consistent orientation for convenient dispensing, while limiting potentially adverse interactions between the adhesive and the container. By avoiding loss of the adhesive components during storage, these assemblies and methods can extend shelf life and provide consistent adhesive handling properties.

15 Claims, 6 Drawing Sheets

Related U.S. Application Data

(60) Provisional application No. 61/639,332, filed on Apr. 27, 2012.

(58) Field of Classification Search
USPC ...... 206/63.5, 438, 368, 369, 477, 478, 480, 206/488; 433/9, 77
See application file for complete search history.

(56) References Cited

U.S. PATENT DOCUMENTS

| | | |
|---|---|---|
| 4,076,872 A | 2/1978 | Lewicki |
| 4,135,868 A | 1/1979 | Schainholz |
| 4,573,569 A | 3/1986 | Parker |
| 4,843,707 A | 7/1989 | Lake et al. |
| 4,863,451 A | 9/1989 | Marder |
| 4,978,007 A | 12/1990 | Jacobs |
| 5,015,180 A | 5/1991 | Randklev |
| 5,172,809 A | 12/1992 | Jacobs |
| 5,183,403 A | 2/1993 | Masuhara |
| 5,221,202 A | 6/1993 | James |
| 5,328,363 A | 7/1994 | Chester |
| 5,350,059 A | 9/1994 | Chester |
| 5,354,199 A | 10/1994 | Jacobs |
| 5,429,229 A | 7/1995 | Chester |
| 5,538,129 A | 7/1996 | Chester |
| 5,575,645 A | 11/1996 | Jacobs |
| 5,827,058 A | 10/1998 | Kelly |
| 6,089,861 A | 7/2000 | Kelly |
| 6,183,249 B1 | 2/2001 | Brennan |
| 6,364,098 B2 | 4/2002 | Yavitz |
| 6,482,003 B2 | 11/2002 | Dixon |
| 6,528,555 B1 | 3/2003 | Nikutowski |
| 6,880,706 B2 | 4/2005 | Braconnot |
| 6,960,079 B2 | 11/2005 | Brennan |
| 7,264,117 B2 | 9/2007 | Atkin |
| 7,381,053 B2 | 6/2008 | Tuneberg |
| 7,726,470 B2 | 6/2010 | Cinader |
| 7,841,464 B2 | 11/2010 | Cinader, Jr. |
| 7,910,632 B2 | 3/2011 | Cinader, Jr. |
| 8,925,719 B2 | 1/2015 | Kesling |
| 2003/0196914 A1 | 10/2003 | Tzou |
| 2008/0044787 A1* | 2/2008 | Cinader, Jr. ............ A61C 7/16 433/9 |
| 2008/0096150 A1 | 4/2008 | Cinader, Jr. |
| 2008/0286710 A1 | 11/2008 | Cinader, Jr. |
| 2009/0233252 A1 | 9/2009 | Cinader, Jr. |
| 2013/0075282 A1 | 3/2013 | Cinader, Jr. |

FOREIGN PATENT DOCUMENTS

| | | |
|---|---|---|
| JP | 01-149646 U | 10/1989 |
| JP | 2-121725 U | 10/1990 |
| JP | 8-140994 | 6/1996 |
| JP | 10-59453 A | 3/1998 |
| JP | 2001-318733 | 11/2001 |
| JP | 2005-239188 A2 | 9/2005 |
| JP | 2011-116415 A | 6/2011 |
| WO | WO 2006-058162 | 6/2006 |
| WO | WO 2008-144123 | 11/2008 |
| WO | WO 2010-126716 | 11/2010 |
| WO | WO 2011-153039 | 12/2011 |
| WO | WO 2012-091902 | 7/2012 |

* cited by examiner

CONTAINER FOR ORTHODONTIC APPLIANCES

CROSS REFERENCE TO RELATED APPLICATIONS

This patent application claims priority to application Ser. No. 14/397,119, filed Oct. 24, 2014, issued as U.S. Pat. No. 9,504,544 on Nov. 29, 2016, which claims priority to U.S. 371 Application No. PCT/US2013/036998, filed on Apr. 17, 2013, which claims priority to U.S. Provisional Application No. 61/639,332, filed Apr. 27, 2012. All of the aforementioned applications are incorporated by reference herein in their entirety.

FIELD

Containers and related methods are provided for appliances and assemblies. More particularly, containers and related methods are provided for storing and dispensing appliances and assemblies used in orthodontic treatment.

BACKGROUND

Orthodontics is the specialized field of dentistry concerned with the treatment of crooked teeth. There are many reasons for obtaining orthodontic treatment, including improvements to facial aesthetics and bite function, and easier maintenance of oral hygiene. A predominant form of orthodontic therapy known as "fixed appliance therapy" involves the use of tiny appliances called brackets, which are bonded to the labial or lingual surfaces of a patient's teeth. Other appliances, called molar tubes, are often affixed to the patient's molar teeth. Each of these appliances has a precisely defined slot or channel for accommodating a resilient arch-shaped wire (or "archwire"). The brackets, molar tubes, and archwire are collectively known as "braces." At the beginning of treatment, the archwire is secured to the slot or channel of each appliance during treatment. While the archwire initially adopts a distorted shape, it gradually returns toward its original shape while straightening the teeth associated with it.

The storage and dispensing of orthodontic brackets, molar tubes, and other appliances before they are bonded to a patient can pose a number of technical challenges. One challenge is inventory management. Most fixed appliances are not universal, and thus differ from tooth to tooth. Additionally, appliances are also differentiated based on the orthodontic prescription and appliance family. For example, brackets with certain slot orientations may be used for some patients but not others, and both ceramic and metal brackets may be used in the same practice. Because orthodontic appliances are tiny, providing a system to manage such an inventory and ensure that the system works efficiently in a busy orthodontic office is not a trivial issue.

Another issue that can affect the efficiency of an orthodontic practice is the time spent preparing a suitable orthodontic adhesive and applying it to the bonding surface of each appliance. Traditionally these were manual steps, but orthodontic product manufacturers have addressed the problem in different ways. For example, 3M Unitek's APC II and APC PLUS Adhesive Coated Appliance System precoats the bonding base of each appliance and packages the coated appliance in a sealed labeled container. These containers can then be arranged on a setup tray, where they are opened immediately prior to bonding by the treating professional.

SUMMARY

Adhesive pre-coated orthodontic appliances are generally stored and handled gently because orthodontic adhesives are tacky and can be inadvertently transferred to the packaging materials without proper care. Such a transfer is usually undesirable because it reduces the amount of adhesive on the appliance when it is placed on the tooth. The problem is further complicated when the components of the adhesive are selectively transferred. For example, over time, a resin component of a paste adhesive may leech out of the adhesive and cause a concentration of the adhesive filler component. The result can be an unpredictable change in the adhesive viscosity and handling characteristics.

While there are various ways to solve this problem, each has notable shortcomings. For example, an adhesive pad may be applied to a bonding base of the appliance and then secured to a porous liner. Such liners, however, tend to absorb a significant degree of resin from the adhesive pad. Alternatively, the adhesive-coated appliance could be suspended in air beneath the tiewings of the bracket to avoid contact between the adhesive and the container. This approach, however, can complicate the technique used to remove the appliance from the container. As yet another option, each appliance could be suspended from a long-axis indicator received in its archwire slot, but this approach introduces a disposable component which must be subsequently removed after bonding, which is wasteful and can be nuisance to the treating professional. Finally, approaches that suspend the bracket often require that different containers be used for different appliance geometries, which can be expensive and impractical for an orthodontic manufacturer.

The provided packaged orthodontic assemblies and methods overcome the above problems by compressively retaining the appliance in the container along opposing sides of the appliance base adjacent the bonding surfaces of the base. This can be done using a mechanism that limits contact between the appliance and the container while accommodating a substantial range of transverse base dimensions. This engagement mechanism allows an adhesive-coated appliance to be retained in a consistent orientation for convenient dispensing to a treating professional, while also limiting potentially adverse interactions between the adhesive and the container. As a result, this solution can extend shelf life and improve the consistency of adhesive handling properties during storage. This approach can also enable a single package to accommodate appliances having significantly different shapes and sizes, thus avoiding the need to customize a container for each bracket type.

In one aspect, a packaged orthodontic assembly is provided. The assembly comprises: an orthodontic appliance having a base for attachment to a tooth; and a container having a recess with a bottom surface and a pair of opposing, non-parallel side surfaces providing an enlarged recess entrance, whereby the side surfaces contact opposing sides of the base to retain the appliance in the recess.

In another aspect, a packaged orthodontic assembly is provided comprising: an orthodontic appliance having a base for attachment to a tooth, the base having a pair of opposing outer edges; and a container having a recess with a bottom surface and a pair of opposing side surfaces, each side surface including a ledge supporting an outer edge of the base operating to suspend the appliance above the bottom wall of the recess.

In still another aspect, a packaged orthodontic assembly is provided, comprising: an orthodontic appliance having a base for attachment to a tooth, the base having a pair of opposing outer edges; and a container having a recess with a bottom surface and a pair of opposing side surfaces, each side surface including a ledge contacting a respective outer edge of the base to suspend the appliance above the bottom wall of the recess.

In yet another aspect, a method of making a packaged orthodontic assembly is provided. The method comprises: providing a container having a recess comprising a bottom surface and a pair of opposing side surfaces having a non-parallel orientation to provide an enlarged recess entrance; placing an orthodontic appliance at least partially within the recess entrance; and urging the appliance toward the bottom surface to compressively retain the appliance along a transverse direction based on contact between the appliance and respective opposing side surfaces.

In yet another aspect, a method of making a packaged orthodontic assembly is provided, comprising: providing a container having a recess comprising a bottom surface and a pair of opposing side surfaces, each side surface having at least one protrusion for engaging a respective side of the appliance; and urging an orthodontic appliance toward the bottom surface to at least partially deform at least one protrusion, the partial deformation of at least one protrusion enabling the appliance to be compressively retained between the side surfaces.

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION

Particular embodiments will now be described in further detail by way of illustration and example. Figures are provided for demonstrative purposes and are not necessarily to scale. Like numerals denote like elements where appropriate.

Figure 1:
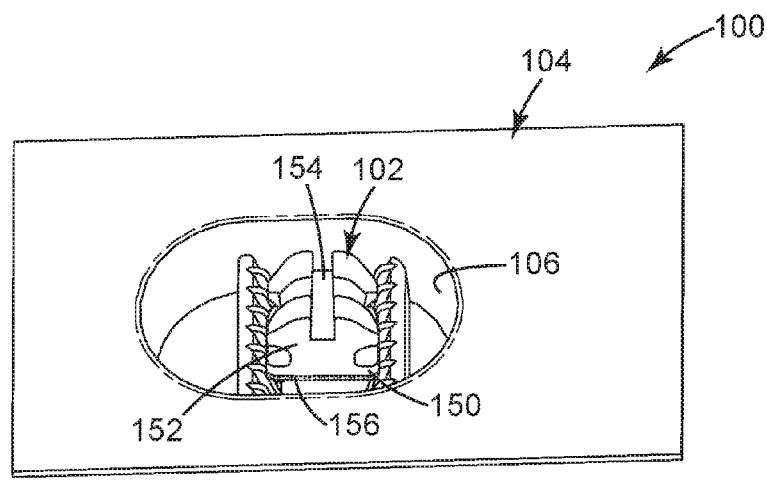
FIG. 1 is a perspective view showing an orthodontic assembly according to one embodiment, looking at its facial, mesial, and occlusal sides.

According to one exemplary embodiment, FIG. 1 shows a packaged orthodontic assembly designated by the numeral 100. The orthodontic assembly 100 includes a container 104 with a recess 106, and an appliance 102 received in the recess 106. In this case, the appliance 102 is an orthodontic bracket having a base 150, a body 152 extending outwardly from the base 150, and an elongated archwire slot 154 extending across a facial surface of the body 152. The base 150 has a bonding surface adapted for attachment to a tooth surface and an adhesive 156 extending across at least a portion of the bonding surface. The appliance 102 is secured to the rest of the assembly 100 by contact between opposing sides of the base 150 and inner surfaces of the container 104.

The container 104 can be made from any of a number of suitable materials known in the art. If the adhesive 156 is light-sensitive, the walls of the container 104 can be made from a suitable light-blocking material, such as a polymeric-metal laminate or metal-filled polymer composite described in U.S. Patent Publication No. 2003/0196914 (Tzou et al.). The container 104 can also be formed using any of a number of known polymer processing methods, such as extrusion, injection molding, or thermoforming. In some embodiments, the polymer composite is based on a resilient thermoplastic such as polypropylene.

While an orthodontic bracket is shown here, it is to be understood that the container 104 could be adapted for use with other orthodontic appliances having a base for bonding to a tooth surface. Such orthodontic appliances may include, for example, molar or bicuspid tubes, buttons, cleats, and sheaths.

Figure 2:
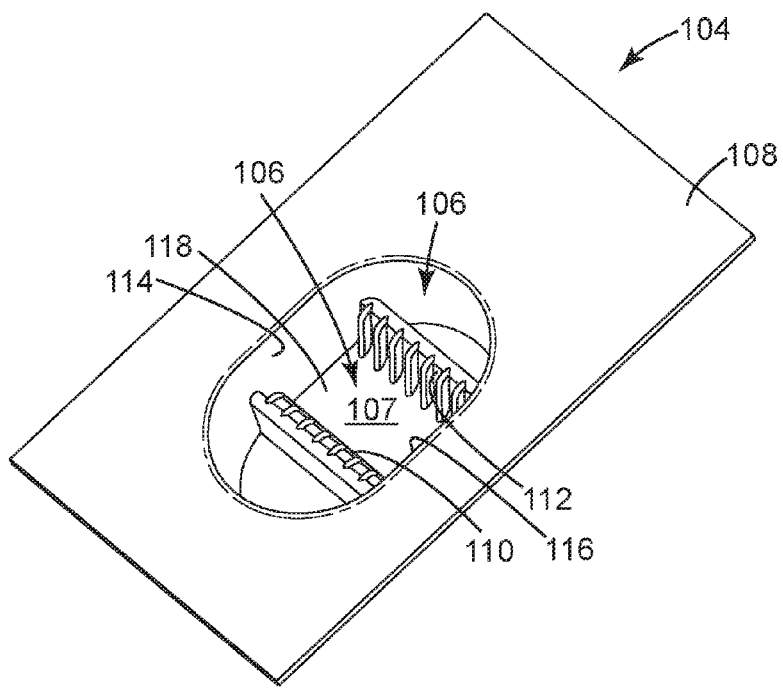
FIG. 2 is a perspective view of a container component of the orthodontic assembly of FIG. 1, looking at its facial, mesial, and occlusal sides.
Figure 3:
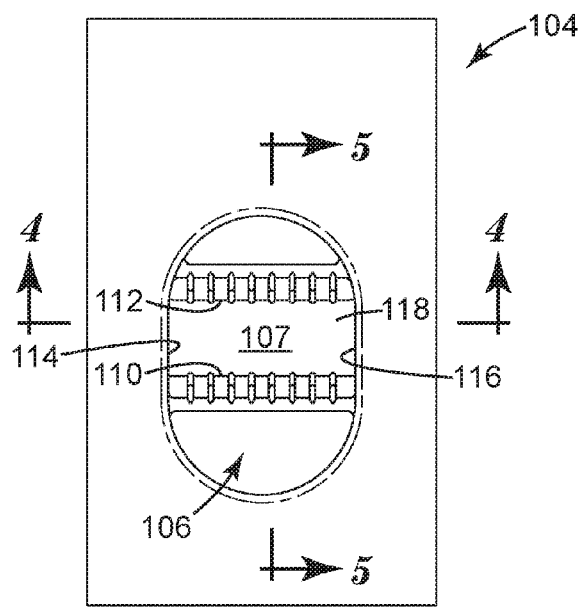
FIG. 3 is a facial view of the container of FIG. 2, looking at its facial side.

FIGS. 2-5 further illustrate particular aspects of the container 104. For improved clarity, the appliance 102 and associated adhesive 156 are not shown in these figures. The container 104 has a substrate 108 and the recess 106 is located in the substrate 108. FIGS. 2-3 show a receiving area 107 for the appliance 102 bounded by a first pair of opposing side surfaces 110, 112, a second pair of opposing side surfaces 114, 116, and a bottom surface 118. The embodiment in FIGS. 2-5 illustrates that the surfaces 110, 112, 114, 116 which bound the receiving area 107 need not be the outermost surfaces of the recess 106. In the container 104 as illustrated, the opposing surfaces 114, 116 are also the outermost surfaces of the recess, while opposing surfaces 110, 112 are not.

Figure 5:
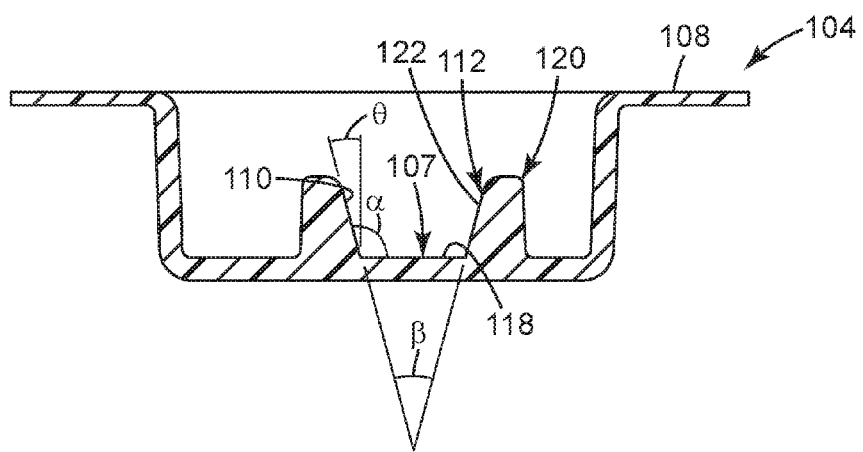
FIG. 5 is a mesial cross-sectional view of the container of FIGS. 2-4 taken along section 5-5 of FIG. 3 and looking at its mesial side.

The first pair of opposing surfaces 110, 112 are non-parallel, and provide a receiving area 107 with a somewhat enlarged entrance. As shown in FIG. 5, the receiving area 107 has a generally trapezoidal shape when viewed from the mesial or distal directions. The second pair of opposing surfaces 114, 116 can also be non-parallel, although they are parallel in this embodiment. Alternatively, the first pair of opposing surfaces 110, 112 can be parallel and the second pair of opposing surfaces 114, 116 can also be parallel. As another option, the bottom surface 118 is generally planar and parallel to areas of the substrate 108 surrounding the recess 106. Each surface 110, 112 has a plurality of discrete rails 120 that are generally parallel to each other and protrude into the receiving area 107. At least some of the rails 120 on each surface 110, 112 are coplanar with reference planes that intersect the appliance 102 when the appliance 102 is seated in the receiving area 107.

Figure 4:
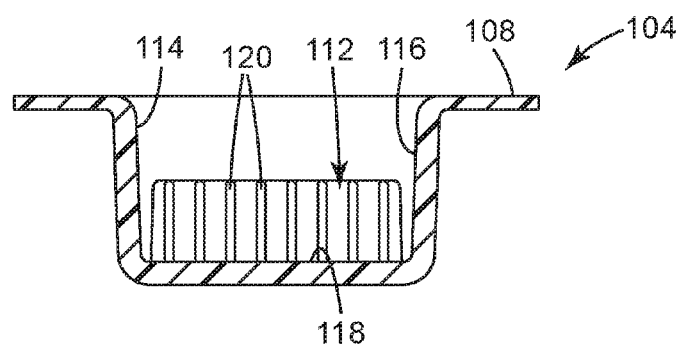
FIG. 4 is an occlusal cross-sectional view of the container of FIGS. 2-3 taken along section 4-4 of FIG. 3 and looking at its occlusal side.

FIG. 4 is a cross-sectional view that shows in greater detail the arrangement of rails 120 along the side surface 112. Within the receiving area 107, eight vertically-aligned rails 120 are evenly spaced along the long dimension of the surface 112. In the configuration shown, the gaps between adjacent rails 120 are approximately four times the width of the rails 120 themselves. Optionally and as shown, a matching set of rails 120 are present on the opposite facing surface 110. If desired, the shape of each rail 120, overall width of each rail 120, and pitch (or spacing) of the rails 120 may be adjusted according to the rail material and type of engagement required by the application at hand. In one preferred embodiment, the rails have an average width of about 0.25 millimeters (0.010 inches) and an average height of about 0.38 millimeters (0.015 inches).

FIG. 5 is another cross-sectional view rotated 90 degrees from that shown in FIG. 4. The cross-section is taken along a reference plane passing through a pair of opposing rails 120 located on respective surfaces 110, 112. This figure also shows the taper in the rails 120, reflecting the taper in the associated surfaces 110, 112 more generally. The taper can be characterized by an angle θ between a normal to the bottom surface 118 and a leading edge 122 of the rail 120, as shown. Although the leading edge 122 is parallel to adjacent portions of the side surface 112 in this embodiment, this need not be the case. For example, the leading edge 122 may have one degree of taper while adjacent portions of the side surface 112 may have another.

As an alternative, the degree of taper can be defined by the obtuse angle α formed between the bottom surface 118 and the leading edge 122, where α=θ+90 degrees in the container configuration shown. As still another alternative, the degree of taper could also be defined based on the orientation of one side surface 110 relative to the opposing side surface 112. In FIG. 5, this angle β formed between these surfaces would be 2θ, although this condition would not necessarily hold true where the side surfaces 110, 112 are not symmetrically disposed.

In some embodiments, the angle θ is at least 5, at least 10, or at least 15 degrees. In some embodiments, θ is at most 45, at least 35, or at least 25 degrees. The angle α can be at least 95 degrees, at least 100 degrees, at least 105 degrees, and can be at most 135 degrees, at most 125 degrees, or at most 115 degrees. Finally, in exemplary embodiments, β is at least 10, at least 20, or at least 30 and is at most 90 degrees, at most 70 degrees, or at most 50 degrees.

Figure 6:
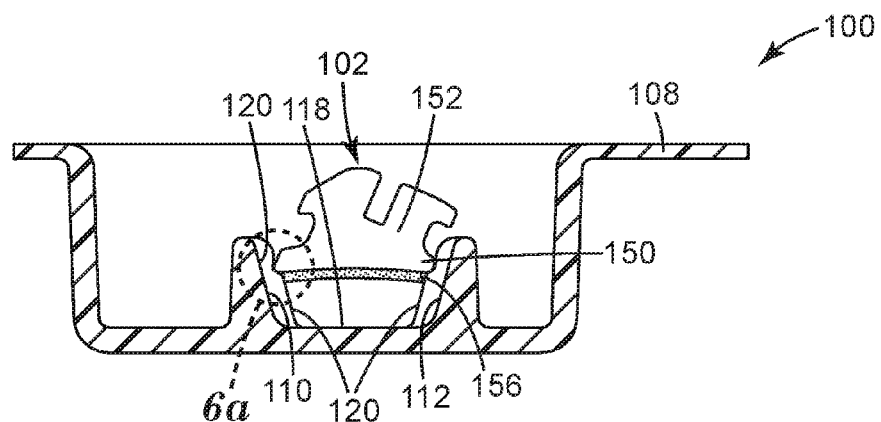
FIG. 6 is a mesial cross-sectional view of the assembly of FIG. 1, looking at its mesial side.
Figure 6A:
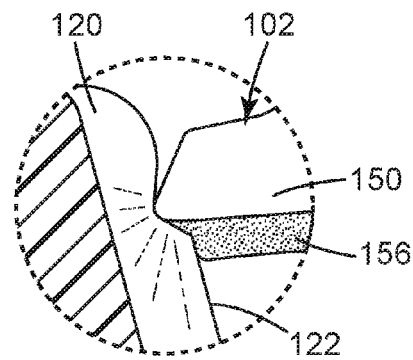
FIG. 6a is an inset showing a magnified view the interaction between components of the assembly of FIG. 6.

FIGS. 6 and 6a show, in more detail, the mechanical interaction between the rails 120 and the appliance 102 when the appliance 102 (in this case coated with an adhesive 156) is placed into the recess 106 and urged toward the bottom surface 118 of the receiving area 107. As mentioned previously, the appliance 102 is secured within the recess 106 of the container 104 by contact between the occlusal-gingival surfaces 110, 112 of the receiving area 107 and the occlusal and gingival sides of the appliance 102. Advantageously, the rails 120 engage opposing sides of the base 150 to compressively retain the appliance 102 in a suspended configuration that avoids contact between the adhesive 156 and the bottom surface 118. In a preferred embodiment, there is an interference fit between the appliance 102 and the plurality of rails 120.

Optionally and as shown, one or more of the rails 120 are at least partially collapsible. In the inset FIG. 6a, the rails 120 are sufficiently soft that the leading edge 122 of each rail 120 compressively deforms upon the urging of the appliance 102 into the receiving area 107 of the recess 106. This deformation, which may be elastic, plastic, or a combination of both, can result in the rails 120 closely conforming with the base 150 of the appliance 102, resulting in a more secure engagement. This is especially useful where there is significant variation amongst the geometries of different appliances. Such variation may be due to differences in base sizes for different brackets, minor defects, or even manufacturing tolerances. By using collapsible protrusions, such as rails 120, it can be possible to afford a configuration for the container 104 that can accommodate a wide variety of appliances 120 in the recess 106.

Alternative configurations are possible. In some embodiments, for example, the container 104 compressively retains the appliance 102 along a transverse direction other than the occlusal-gingival direction. For example, the opposing surfaces 114, 116, which face in the generally mesial and distal directions, could engage respective mesial and distal sides of the appliance 102. As a further alternative, the four surfaces 110, 112, 114, 116 could simultaneously engage all four sides of the appliance 102 when the appliance 102 is seated in the container 104. Occlusal-gingival engagement is generally preferred, however, because orthodontic appliances tend to show less variation in occlusal-gingival height compared with mesial-distal width. Additionally, maintaining an open space adjacent the mesial and distal sides of the appliance 102 provides locations where a treating professional can access the appliance 102 with tweezers or some other hand instrument.

As a result of the mechanical engagement between the appliance 102 and the rails 120, the appliance 102 is suspended in a fixed position above the bottom surface 118. In this position, the appliance 102 and its associated adhesive are vertically spaced apart from the bottom surface 118, thus avoiding substantial contact between the adhesive and the container 104. Other features of the container 104 can also affect the extent of contact. For example, as shown in FIGS. 3-4, the leading edge 122 of each rail 120 has a somewhat pointed, blade-like geometry. This aspect can further limit the contact between the appliance 102 and the container 104 when the appliance 102 is seated in the recess 106. As an alternative to the rails 120 illustrated here, it is also possible to use prongs, bumps, or other protrusions on one or both side surfaces 110, 112 to achieve the same or a similar function.

Certain unexpected advantages derive from limited contact between the appliance 102 and the container 104. First, reducing interfacial contact has the effect of deceasing surface area along which adhesive components can wick away from the base 150 of the appliance 102. This is especially beneficial when dealing with heterogeneous adhesives, for example adhesives that have an unhardened dental composition absorbed into a compressible material, as described in U.S. Patent Publication No. 2009/0233252 (Cinader). Loss of certain components, for example initiators such as camphorquinone, can have detrimental effects on adhesive shelf life and cause aspects of adhesive texture, such as viscosity, to change during long storage periods. Second, decreased interfacial contact generally results in the base 150 applying greater compressive stress to the side surfaces 110, 112 when the appliance 102 is seated into the receiving area 107. Since this compressive stress is reciprocated in a state of equilibrium by the walls defining the surfaces 110, 112, the walls of the container 104 can more readily deform against the appliance 102, resulting in a more secure grip on the appliance 102.

The tapered side surfaces 110, 112 in FIGS. 2-6 provide additional advantages. First, the presence of a taper in the surfaces 110, 112 can even further reduce the interfacial area between the base 150 and the leading edge 122 of the rails 120 by limiting contact to the corner of the base 150 adjacent the bonding surface, as shown in FIG. 6a. This reduces the opportunity for loss of the adhesive or adhesive components. Second, a slight taper provides a mechanical advantage that enables deformation of the collapsible rails 120 when the appliance 102 is pressed into the receiving area 107. This, in turn, can provide a more conformal and secure retention of the appliance 102 as described earlier. Third, the taper allows the receiving area 107 to be "universal," accommodating appliances having a wide variety of sizes and shapes. The result is a reduction in manufacturing costs, since the same container geometry can be used to package orthodontic appliances having different occlusal-gingival heights, for different teeth, and even between different appliance families.

The totality of the above features can help minimize adhesive loss when the appliance 102 is plucked from the container 104 during an orthodontic bonding procedure. In some embodiments, the adhesive loss is at most 2 percent, at most 5 percent, or at most 20 percent of the original coating weight of the adhesive 156 on the base 150 of the appliance 102. In a preferred embodiment, essentially all of the adhesive 156 is maintained on the base 150 when the appliance 102 is dispensed from the container 104.

Figure 7:
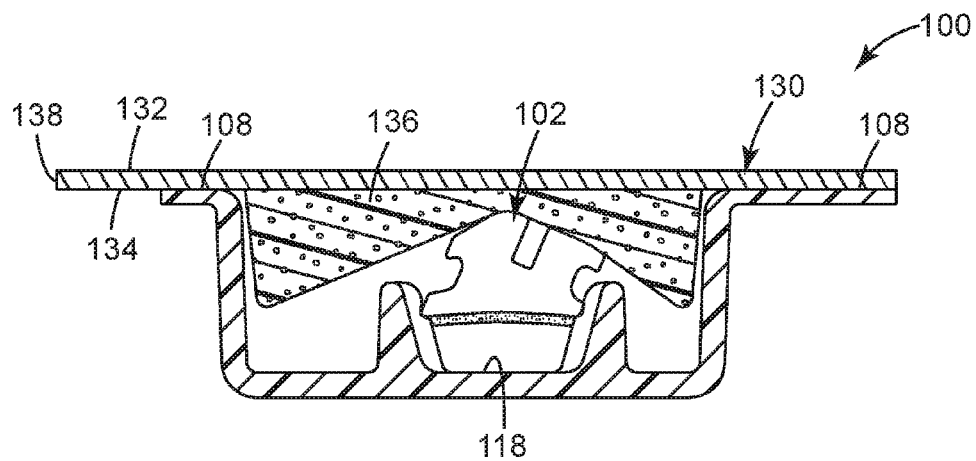
FIG. 7 is a mesial cross-sectional view of a lidded orthodontic assembly according to another embodiment, looking at its mesial side.
Figure 8:
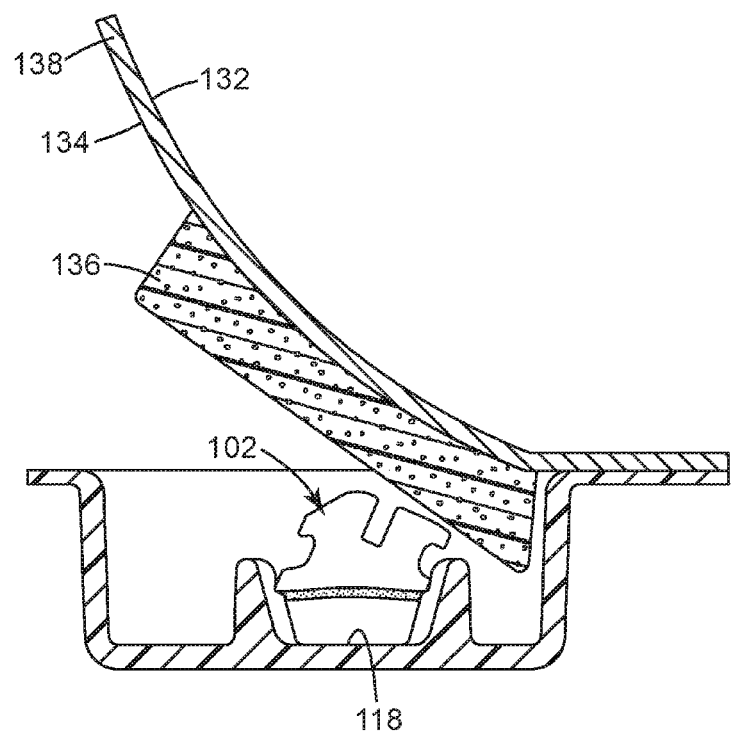
FIG. 8 is mesial cross-sectional view of the assembly of FIG. 7, looking at its mesial side and with the lid partially opened.
Figure 9:
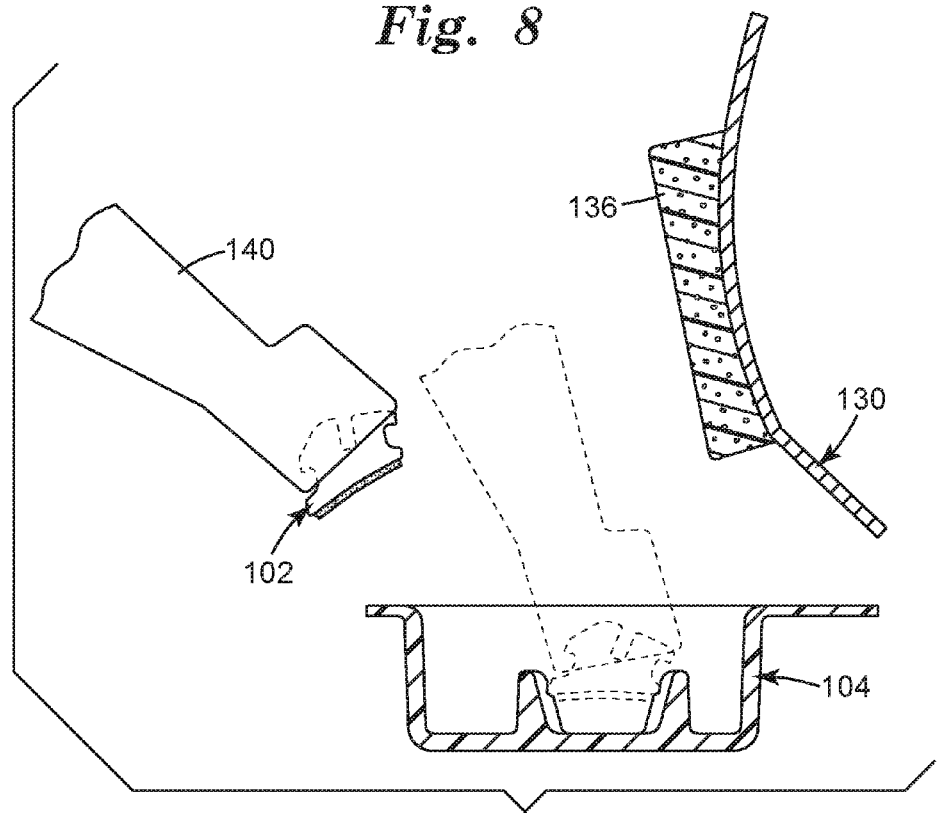
FIG. 9 is a mesial cross-sectional view of the assembly of FIGS. 7-8, looking at its mesial side while as an appliance of the assembly is being dispensed.

An optional feature of the assembly 100 is shown in FIGS. 7-9. First, referring to FIG. 7, the assembly 100 has a removable lid 130 (or cover) that extends over the opening of the recess 106 to isolate the appliance 102 from the external environment. The lid 130 has a top surface 132 and a bottom surface 134, and may or may not be hermetically sealed along the interface between the bottom surface 134 and the areas of substrate 108 surrounding the recess 106. The lid 130 extends beyond the substrate 108 on one side, resulting in a tab 138. Suitable lidding materials may include light-blocking materials such as, for example, laminates with a thermoplastic layer, a metallic layer, and a heat seal coating, as described in U.S. Patent Publication No. 2003/0196914 (Tzou et al.).

Also illustrated in FIG. 7, a compressible member 136 is secured to the bottom surface 134 of the lid 130, the member 136 residing in the recess 106 when the lid 130 is in its closed position. The member 136 contacts the facial surface of the appliance 102 (opposite the base 150) and provides an additional safeguard to prevent the appliance 102 from moving (or "skating") significantly in directions perpendicular to the bottom surface 118 or alternatively "tipping over" within the receiving area 107. Advantageously, the member 136 can prevent the appliance 102 from becoming dislodged from the receiving area 107 when the assembly 100 is subjected to shock and vibration. Optionally and as shown, the member 136 contacts one or more surfaces of the appliance 102 at a non-zero angle relative to the bottom surface 118 of the receiving area 107 to help prevent the appliance 102 from sliding laterally in the receiving area 107.

The member 136 decreases in volume and conform to facial surfaces of the appliance 102 in response to compressive forces that result from closing the lid 130 over the recess 106. Depending on its stiffness, the member 136 could also assist in securing the appliance 102 by applying a continuous, positive force to urge the appliance 102 toward the bottom surface 118 of the receiving area 107. Although not shown, the side of the member 136 that engages the appliance 102 can optionally have a generally concave shape when relaxed. Such a configuration could be complementary with at least a portion of the facial side of the appliance 102 and avoid excessive compression of the member 136 when the lid 130 is closed.

Various compressible materials can be used to construct the member 136, including soft porous, polymeric open-celled and closed-cell foams, woven and non-woven materials. Preferred foam materials include ethylene propylene diene monomer and crosslinked polyethylene. In an exemplary embodiment, the member 136 has a compression deflection at 25 percent at a pressure of at most 14 kilopascals (2 pounds per square inch). Further options and advantages associated with packaged assemblies including compressible members are described in provisional U.S. Patent Application Ser. No. 61/350,623 (Cinader, et al.).

FIG. 8 shows the opening of the lid 130 by pulling on the tab 138 in an upward, peeling motion resulting in the bottom surface 134 becoming separated from the underlying surfaces of the substrate 108. As shown, the member 136 pulls away from the appliance 102, causing the member 136 to spring back toward its original, relaxed shape. In some embodiments, the lid 130 is completely removed from the substrate 108 as depicted in FIG. 9, providing open access to the recess 106 and the appliance 102 during a bonding procedure. As further illustrated in FIG. 9, a treating professional can then grip and remove the appliance 102 from the container 104 using, for example, a suitable hand instrument 140.

Figure 10:
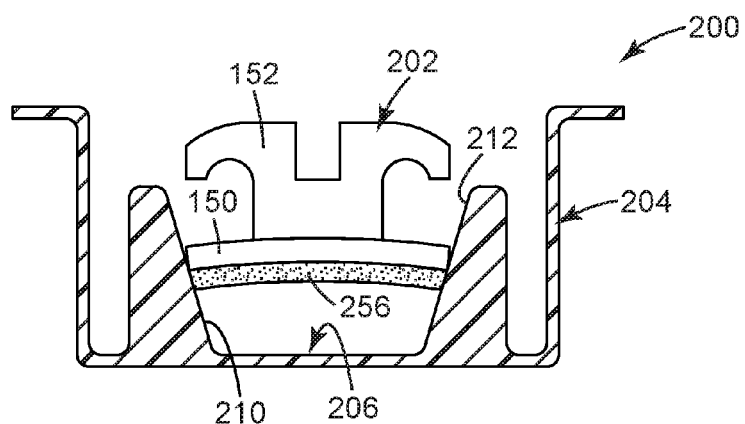
FIG. 10 is a mesial cross-sectional view of an assembly according to still another embodiment, looking at its mesial side.

FIG. 10 show an alternative assembly 200, in which an appliance 202 having a body 252 and a base 250 coated with an adhesive 256 is secured in a recess 206 of a container 204. The container 204 has generally opposing side surfaces 210, 212 that are tapered relative to each other. The container 204 differs from those of previous embodiments in that the surfaces 210, 212 do not include rails or any other protrusions to limit the contact between the appliance 202 and the container 204. Instead, the taper in the surfaces 210, 212 assists in limiting contact of these components with each other to a narrow corner region extending along opposing sides of the base 250. As described in previous embodiments, the walls in the container 204 defining the surfaces 210, 212 apply compressive force to the base 250 to retain the appliance 202 in the recess 206.

Figure 11:
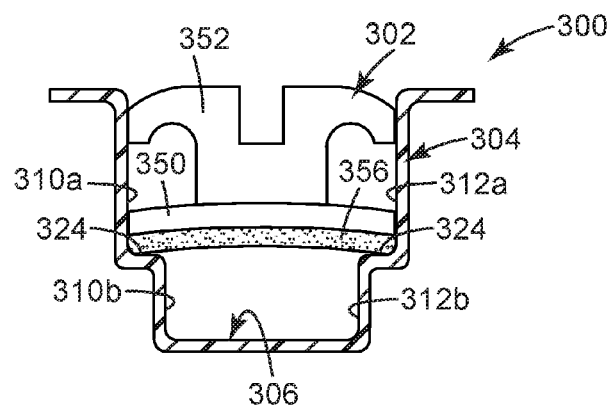
FIG. 11 is mesial cross-sectional view of an orthodontic assembly according to yet another embodiment, looking at its mesial side.

FIG. 11 shows a packaged assembly 300 according to still another embodiment. The assembly 300 includes a container 304 with a recess 306, and an appliance 302 received in the recess 306. As before, the appliance 302 has a base 350, a body 352 extending outwardly from the base 350, and an adhesive 356 extending across a bonding surface of the base 350. It is to be understood that only a partial view is shown and other aspects of the assembly 300 are similar to those previously described for assemblies 100, 200.

The assembly 300 differs from the assemblies 100, 200 in that the container 304 does not engage the appliance 302 along tapered side surfaces. Instead, the container 304 has a pair of ledges 324 upon which the appliance 302 rests. Optionally and as shown, the ledges 324 are generally parallel to, and spaced apart from, a bottom surface 318 of the recess 306. The ledges 324 contact portions of the adhesive 356 extending along the outer edge of the base 350 to suspend the appliance 302 and its associated adhesive 356 above the bottom surface 318. The recess 306 further includes a first pair of side surfaces 310a, 312a extending along the ledges 324 and contacting opposing sides of the base 350 to prevent lateral movement of the appliance 302 within the recess 306. A second pair of side surfaces 310b, 312b extends below the ledge, but does not come into contact with the base 350.

While FIG. 11 shows the appliance 302 supported by virtue of the adhesive 356 contacting the ledges 324, it is also possible for the ledges 324 to support the appliance base 350 without any interposing structure. For example, where the adhesive coats only a center portion of the bonding surface of the base 350 or is absent entirely, the outer edges of the base 350 of the appliance 302 can rest directly against the ledges 324. This type of configuration can be beneficial, for instance, where essentially zero contact between the adhesive 356 and the container 304 is desired.

In a preferred embodiment, the ledges 324 are as narrow as possible to avoid substantial contact between the adhesive 350 and the container 304, thereby reducing the surface area along which adhesive components could be lost during storage and/or transport. In some cases, however, it may be desirable for the ledges 324 to be made broader, particularly if a plurality of appliances having disparate base sizes are to be accommodated in the same container configuration. As another possibility, some or all of the ledges 324 or side surfaces 310a, 310b may also be tapered as previously described to reduce the contact area between the appliance 302 and the container 304.

Figure 12:
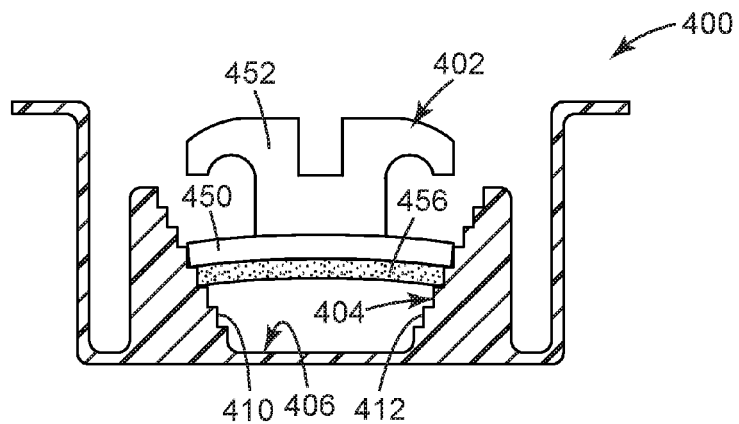
FIG. 12 is mesial cross-sectional view of an orthodontic assembly according to yet another embodiment, looking at its mesial side.

FIG. 12 shows an assembly 400 combining beneficial characteristics of both assemblies 200 and 300. The appliance 402 has a body 452 extending from a bonding base 450, and an adhesive 456 extends along at least a portion of the bonding surface of the base 450. Once again, the appliance 402 is received in the recess 406 of a container 404 having opposing surfaces 410, 412. In this embodiment, however, the surfaces 410, 412 have a "stair-step" configuration with alternating horizontal and vertical edges provided at a fine scale. As a result, the surfaces 410, 412 are functionally tapered on a macroscopic scale, while parallel on a microscopic scale. Like other tapered configurations, the use of a stair-step pattern can enable the container 404 to accommodate a range of base sizes, but provides the added benefit of creating a "positive stop" against the horizontal edges of the surfaces 410, 412 when seating the appliance 402 in the recess 406. Having a positive stop, in turn, helps avoid over-compressing the appliance 402 in the container 404, which could lead to difficulties in removal. The stair-steps may also be radiused to reduce the likelihood of the appliance 402 inadvertently slipping past one of the surfaces 410, 412 and disengaging from the container 404.

Figure 13:
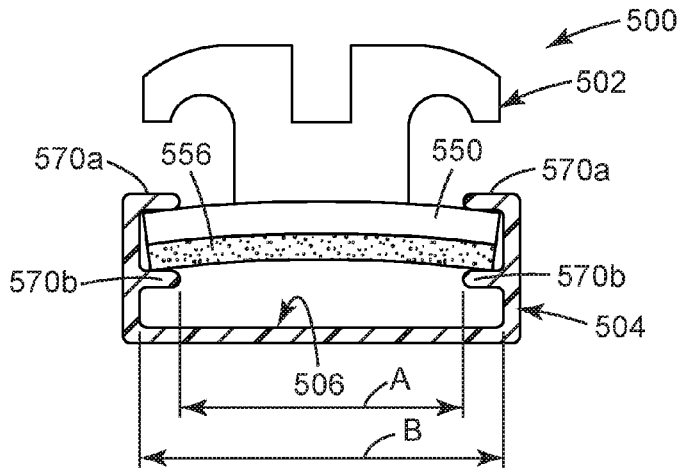
FIG. 13 is mesial cross-sectional view of an orthodontic assembly according to yet another embodiment, looking at its mesial side.

A further variant is provided in FIG. 13, which shows an assembly 500 with an appliance 502 and container 504. The appliance 502 resides in a recess 506 of the container 504 and is essentially identical to appliances previously described. The container 504 includes upper and lower openings 570a, 570b extending along the perimeter of the recess 506. Each opening 570a, 570b has an inner diameter "A" (or inner transverse dimension "A") that is slightly smaller than the outer diameter "B" (or outer transverse dimension "B") of a base 550 of the appliance 502. Because the base 550 is oversized compared with the inner diameter of the openings 570a, 570b, the openings 570a, 570b abut the upper and lower edges of the base 550, thereby retaining the appliance 502 in a fixed vertical position within the recess 506. In preferred embodiments, the openings 570a, 570b are sufficiently thin that a treating professional can easily engage or disengage the appliance 502 from the openings 570a, 570b by gently urging the appliance downward or upward with a suitable hand instrument.

Figure 14:
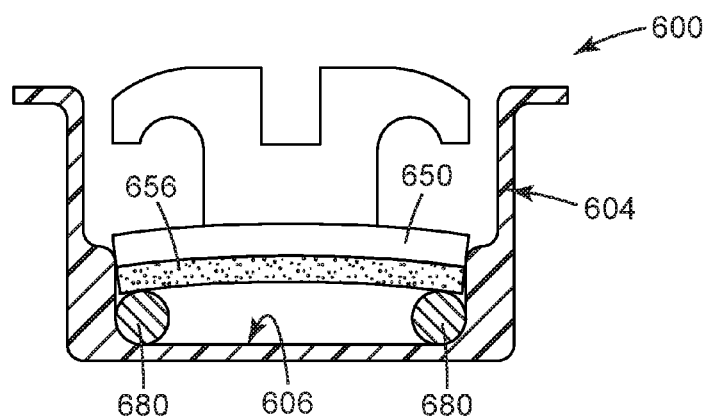
FIG. 14 is mesial cross-sectional view of an orthodontic assembly according to yet another embodiment, looking at its mesial side.

Still another variant is shown in assembly 600 of FIG. 14, in which an appliance 602 contacts the top edge of at least one wire strand 680 that functions as a spacer between a base 650 of the appliance 602 and the bottom surface of a recess 606 located in a container 604. In this embodiment, an adhesive 656 extends across the base 650 of the appliance 602 and rests upon the strand 680 to suspend the appliance 602 within the recess 606. As shown here, opposing sides of the base 650 also contact the side surfaces of the recess 606, although this need not be the case.

Figure 15:
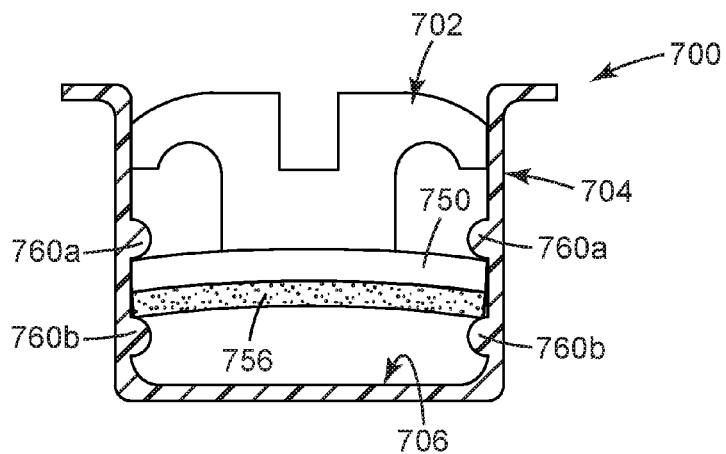
FIG. 15 is mesial cross-sectional view of an orthodontic assembly according to yet another embodiment, looking at its mesial side.

FIG. 15 shows yet another assembly 700 that includes an appliance 702 having a bonding base 750 and retained in a recess 706 of a container 704. In this embodiment, opposing walls of the recess 706 include a plurality of upper and lower bumps 760a, 760b that collectively engage the outer edges of the base 750 to suspend the appliance 702 above the bottom surface of the recess 706. To initially seat the appliance 702 in the container 704, the appliance 702 can be urged into the recess 706, causing opposing walls of the recess 706 to be deflected away from each other and allowing the base 750 to lodge between the upper and lower bumps 760a, 760b. The reverse action can be used to remove the appliance 702 from the recess 706. The force required to engage and disengage the appliance 702 can be adjusted based on the size or shape of the bumps 760a, 760b and the stiffness of the recess walls.

EMBODIMENTS

1. A packaged orthodontic assembly comprising: an orthodontic appliance having a base for attachment to a tooth; and a container having a recess with a bottom surface and a pair of opposing, non-parallel side surfaces providing an enlarged recess entrance, whereby the side surfaces contact opposing sides of the base to retain the appliance in the recess.
2. The assembly of embodiment 1, wherein each side surface forms an obtuse angle relative to the bottom wall ranging from 95 to 135 degrees.
3. The assembly of embodiment 2, wherein the obtuse angle ranges from 100 to 125 degrees.
4. The assembly of embodiment 3, wherein the obtuse angle ranges from 105 to 115 degrees.
5. The assembly of embodiment 1, wherein each side surface has at least one protrusion for engaging a respective side of the appliance, the at least one protrusion being at least partially collapsed.

6. The assembly of embodiment 5, wherein the at least one protrusion comprises at least one rail that, when relaxed, is generally coplanar with a reference plane intersecting the appliance.
7. The assembly of embodiment 1, wherein the side surfaces have a stair-step configuration.
8. A packaged orthodontic assembly comprising: an orthodontic appliance having a base for attachment to a tooth; and a container having a recess with a bottom surface and a pair of opposing side surfaces, each side surface having at least one collapsible protrusion contacting a respective side of the appliance to retain the appliance in the recess, each protrusion being generally coplanar with a respective reference plane intersecting the appliance.
9. A packaged orthodontic assembly comprising: an orthodontic appliance having a base for attachment to a tooth, the base having a pair of opposing outer edges; and a container having a recess with a bottom surface and a pair of opposing side surfaces, each side surface including a ledge supporting an outer edge of the base operating to suspend the appliance above the bottom wall of the recess.
10. The assembly of embodiment 1 or 8, further comprising an adhesive extending across at least a portion of the base.
11. The assembly of embodiment 10, wherein the adhesive comprises a compressible material.
12. The assembly of embodiment 11, wherein the adhesive further comprises an unhardened dental composition absorbed into the compressible material.
13. The assembly of embodiment 1, 8, or 9, wherein the container is made from a resilient polymer.
14. The assembly of embodiment 1, 8, or 9, wherein the appliance is retained in the recess by an interference fit.
15. The assembly of embodiment 1, 8, or 9, wherein the side surfaces contact the occlusal and gingival sides of the base.
16. The assembly of embodiment 15, wherein the side surfaces of the container contact the base at a location where the occlusal-gingival dimension of the base is largest.
17. The assembly of embodiment 1, 8, or 9, further comprising a lid extending across at least a portion of the recess.
18. The assembly of embodiment 17, wherein the lid comprises a compressible member contacting a side of the appliance opposite that of the base to restrain movement of the appliance in directions perpendicular to the bottom surface.
19. A method of making a packaged orthodontic assembly comprising:
providing a container having a recess comprising a bottom surface and a pair of opposing side surfaces having a non-parallel orientation to provide an enlarged recess entrance;
placing an orthodontic appliance at least partially within the recess entrance; and
urging the appliance toward the bottom surface to compressively retain the appliance along a transverse direction based on contact between the appliance and respective opposing side surfaces.
20. The method of embodiment 19, wherein each side surface comprises at least one collapsible protrusion that engages a side of the appliance.
21. A method of making a packaged orthodontic assembly comprising: providing a container having a recess comprising a bottom surface and a pair of opposing side surfaces, each side surface having at least one protrusion for engaging a respective side of an orthodontic appliance; and urging an orthodontic appliance toward the bottom surface to at least partially deform at least one protrusion, the partial deformation of at least one protrusion enabling the appliance to be compressively retained between the side surfaces.
22. The method of embodiment 19 or 21, wherein the appliance has a base for attachment to a tooth and the assembly further comprises an adhesive extending across at least a portion of the base, the at least one protrusion reducing contact between the adhesive and the container whereby substantially all of the adhesive is maintained on the base when the appliance is dispensed from the container.
23. A method of making a packaged orthodontic assembly comprising: providing a container having a recess comprising a bottom surface and a pair of opposing side surfaces, each side surface having a ledge generally parallel to the bottom surface and spaced apart from the bottom surface; and placing an orthodontic appliance in the recess wherein either a base of the appliance, or an adhesive disposed thereon, flatly engages the ledges to suspend the appliance above the bottom surface, wherein the side surfaces contact opposing sides of the base to prevent lateral movement of the appliance within the recess.

EXAMPLES

Objects and advantages of this invention are further illustrated by the following examples. While particular materials and amounts thereof are provided herein, these should not be construed to unduly limit this invention. Unless otherwise noted, all parts and percentages are on a weight basis and all molecular weights are weight average molecular weight. Also unless otherwise noted, all solvents and reagents were obtained from Aldrich Chemical Company in Milwaukee, Wis.

Appliance Preparation

Adhesive-coated appliances were based on CLARITY brand SL brackets (3M Unitek, Monrovia, Calif.). Four different bracket types were tested, including lower anterior, lower bicuspid, upper central, and upper cuspid brackets. After procurement, the bonding surface of each bracket was coated with an adhesive that incorporates a compressible material, as generally described by Example 1 of U.S. Patent Application Ser. No. 61/428,498 (Cinader et al.), filed on Dec. 30, 2010.

Container Preparation

The containers in this test were manufactured by injection molding a polypropylene homopolymer resin (ExxonMobil Chemical, Houston, Tex.) compounded with a silver colorant. The lidding is a laminate foil, with a sealing layer of polypropylene. After the appliance was placed in the recess of the container, the lidding was placed over the recess and sealed against the container using a standard heat sealing machine.

In some of the Examples, a separate foam piece was attached to the lidding such that the foam applied slight positive pressure urging the appliance toward the bottom surface of the container when the lidding was closed. The foam attached to the lid is made of soft crosslinked polyethylene (Sekisui Alveo AG, Lucerne, Switzerland). The shape is oval, to match the blister shape, it is undersized to the dimensions of the blister itself. The foam is adhered to the lid via heat sealing machine (the polypropylene layer on the lid is melted to the polyethylene foam) with appropriate fixturing to align the foam. This is done in a process prior to heat sealing the lid to the blister.

Example 1 of U.S. Patent Publication No. 2003/0196914 (Tzou, et al.)) for approximately 24 hours at ambient temperatures.

TABLE 1

Measured resin loss upon removing orthodontic appliances from their container

| Example | n | Bracket type/ lidding | Coating weight (mg) | Adhesive loss (mg) | Adhesive loss (%) | Notes |
|---|---|---|---|---|---|---|
| 1 | 18 | Lower anteriors/ foam lidding | 3.08 | 0.15 | 5.3% | Resin remaining on bottom (3 samples) |
| 2 | 16 | Lower anteriors/ plain lidding | 3.09 | 0.16 | 5.5% | Resin remaining on bottom (4 samples) |
| 3 | 18 | Lower bicuspids/ foam lidding | 4.58 | 0.11 | 2.4% | Resin remaining on bottom (7 samples) |
| 4 | 8 | Lower bicuspids/ plain lidding | 4.60 | 0.07 | 1.6% | Resin remaining on bottom (1 sample) |
| 5 | 14 | Upper central/ foam lidding | 4.80 | 0.12 | 2.7% | Resin remaining on bottom (1 sample) |
| 6 | 13 | Upper central/ plain lidding | 4.81 | 0.06 | 1.3% | Resin remaining on bottom (1 sample) |
| 7 | 20 | Upper cuspids | 4.61 | 0.05 | 1.2% | |
| 8 | 8 | Upper cuspids | 4.63 | 0.06 | 1.2% | |
| CE-1 | 19 | Upper central | 5.34 | 0.61 | 11.3% | |
| CE-2 | 33 | Lower anteriors | 3.14 | 0.28 | 8.7% | |

Resin Loss Measurement

The resin loss calculations were obtained using the following procedure.
1) Three gravimetric measurements were taken to obtain the data:
   a) First, the bare bracket was weighed, and then coated with the adhesive.
   b) Second, the bracket and adhesive were weighed together and stored in a container for an extended period of time.
   c) Third, the bracket and adhesive removed from the container and weighed again.
2) The difference between measurement b) and measurement c) above was defined as the "adhesive loss."
3) Steps 1 and 2 above were repeated as needed to provide measurements on at least 8 replicated packaged appliances (i.e., n≥8).

Examples 1-8 and Comparatives CE-1 and CE-2

The average levels of adhesive loss obtained for four different bracket types were determined using the Resin Loss Measurement procedure above and presented in Table 1. As shown in the Table, Examples 1-8 include packaged lower anterior brackets, lower bicuspid brackets, upper central brackets, and upper cuspid brackets, where each bracket was stored in a container having either a foam lidding or plain lidding. Each package then underwent ship testing per ASTM D-4149. All of Examples 1-8 were stored in the container for at least 1 week and in some cases, up to 3 weeks. In some cases, as noted, adhesive resin was observed on the bottom surface of the container after removal of the bracket.

Comparatives CE-1 and CE-2 represent upper central and lower anterior brackets, respectively, that were coated with adhesive and then placed flatly upon the horizontal bottom surface of a plain, unlined container (such as described in All of the patents and patent applications mentioned above are hereby expressly incorporated into the present disclosure. The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

The invention claimed is:

1. A packaged orthodontic assembly comprising:
   an orthodontic appliance having a base for attachment to a tooth and a body, wherein the base comprises an occlusal side and a gingival side;
   an adhesive extending across at least a portion of the base; and
   a container defining a recess with a bottom surface and a pair of opposing, non-parallel side surfaces providing an enlarged recess entrance, whereby the opposing, non-parallel side surfaces contact the occlusal side and the gingival side of the base at a location where an occlusal-gingival dimension of the base is largest to retain the orthodontic appliance in the recess such that the orthodontic appliance is suspended above the bottom surface.

2. The assembly of claim 1, wherein each opposing, non-parallel side surface forms an obtuse angle relative to the bottom surface ranging from 95 to 135 degrees.

3. The assembly of claim 2, wherein the obtuse angle ranges from 100 to 125 degrees.

4. The assembly of claim 1, wherein each opposing, non-parallel side surface has at least one protrusion for engaging a respective side of the orthodontic appliance, the at least one protrusion being at least partially collapsed.

5. The assembly of claim 4, wherein the at least one protrusion comprises at least one rail that, when relaxed, is generally coplanar with a reference plane intersecting the orthodontic appliance.

6. The assembly of claim 1, wherein the opposing, non-parallel side surfaces each taper between the recess entrance and the bottom surface.

7. The assembly of claim 1, wherein the adhesive comprises a compressible material and an unhardened dental composition absorbed into the compressible material.

8. The assembly of claim 1, wherein the orthodontic appliance is retained in the recess by an interference fit.

9. The assembly of claim 1, wherein the opposing, non-parallel side surfaces include a taper defined based on the orientation of one side surface relative to the opposing side surface, and wherein an angle formed between the side surface and the opposing side surface is at least 10 and no greater than 90 degrees.

10. The assembly of claim 9, and further comprising a lid extending over the recess, wherein the lid comprises a compressible member contacting a surface of the orthodontic appliance opposite that of the base to restrain movement of the orthodontic appliance in directions perpendicular to the bottom surface.

11. A packaged orthodontic assembly comprising:
an orthodontic appliance having a base for attachment to a tooth and a body;
an adhesive extending across at least a portion of the base; and
a container defining a recess with a bottom surface and a pair of opposing, non-parallel side surfaces providing an enlarged recess entrance, whereby the opposing, non-parallel side surfaces contact opposing sides of the base to retain the appliance in the recess such that the appliance is suspended above the bottom surface, and wherein each opposing, non-parallel side surface has at least one protrusion for engaging a respective side of the orthodontic appliance, the at least one protrusion being at least partially collapsed.

12. The assembly of claim 11, wherein the at least one protrusion comprises at least one rail that, when relaxed, is generally coplanar with a reference plane intersecting the orthodontic appliance.

13. The assembly of claim 11, wherein each opposing, non-parallel side surface forms an obtuse angle relative to the bottom surface ranging from 95 to 135 degrees.

14. The assembly of claim 13, wherein the obtuse angle ranges from 100 to 125 degrees.

15. The assembly of claim 11, wherein the adhesive comprises a compressible material and an unhardened dental composition absorbed into the compressible material.

* * * * *